United States Patent [19]
Takayama et al.

[11] Patent Number: 5,910,303
[45] Date of Patent: *Jun. 8, 1999

[54] AGENT FOR PROMOTING THE PLATELET AND THE LEUKOCYTE PRODUCTIONS

[75] Inventors: Kazue Takayama; Akira Harashima; Tsunetaka Ohta; Noboru Izumi; Hiroyoshi Tahata; Masashi Kurimoto, all of Okayama, Japan

[73] Assignee: Kabushiki Kaisha Hayashibara Seibutsu Kagaku Kenkyujo, Okayama, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/570,944

[22] Filed: Dec. 12, 1995

[30] Foreign Application Priority Data

Dec. 16, 1994 [JP] Japan .................................. 6-333684
Dec. 16, 1994 [JP] Japan .................................. 6-333686

[51] Int. Cl.⁶ .......................... A61K 38/19; A61K 38/20; A61K 38/21
[52] U.S. Cl. ........................ 424/85.1; 424/85.2; 424/85.5
[58] Field of Search ................... 424/85.1, 85.2, 424/85.5, 539; 530/351

[56] References Cited

U.S. PATENT DOCUMENTS

| | | | |
|---|---|---|---|
| 5,032,396 | 7/1991 | Williams | 424/85.2 |
| 5,126,325 | 6/1992 | Kishimoto et al. | 514/12 |
| 5,151,265 | 9/1992 | Hwang-Felgner et al. | 424/85.5 |
| 5,178,857 | 1/1993 | Goeth et al. | 424/85.5 |
| 5,358,708 | 10/1994 | Patel | 424/85.1 |
| 5,472,867 | 12/1995 | Kanz et al. | 435/240.25 |
| 5,556,620 | 9/1996 | Ralph et al. | 514/12 |

FOREIGN PATENT DOCUMENTS

| | | |
|---|---|---|
| 0353910 | 2/1990 | European Pat. Off. |
| 8800206 | 1/1988 | WIPO |

OTHER PUBLICATIONS

Weiner, L.M. et al "Tumor Immunology", Proceedings of Asso., vol. 12, Mar. 1993.

Shiohara M. et al. "Synergism of Interferon–Gamma and Stem Cell Factor on the Development of Murine Hematopoietic Progenitors in Serum–Free Culture", Blood, vol. 81, No. 6, Mar. 15, 1993 pp. 1435–1441.

Zoumbos N.C. et al. "Different Haematopoietic Growth Factors Have Different Capacity in Overcoming the in vitro Interferon Gamma–Induced Suppression of Bone Marrow Progenitor Cells", European Journal of Haematology vol. 44, No. 5, May 1990 pp. 282–290.

Barclay A.N. et al. "The Leucocyte Antigen Facts Book", 1992, Hartcourt Brace Jovanovich, London, p. 4, pp. 176–177.

Avraham, Hava. "Regulation of Megakaryocytopoiesis", Stem Cells, vol. 11, pp. 499–510 (1993).

Nand, Sucha, et al., "A Phase I/II Study of Sequential Interleukin–3 and Granuloycte–Macrophage Colony–Stimulating Factor in Myelodysplastic Syndromes", Blood, vol. 83, No. 2, pp. 357–360 (Jan. 15, 1994).

Ogawa, Makio. "Differentiation and Proliferation of Hematopoietic Stem Cells", Blood, vol. 81, No. 11, pp. 2844–2853 (Jun. 1, 1993).

Kishimoto, Tadamitsu. "The Biology of Interleukin–6", Blood, vol. 74, No. 1, pp. 1–10 (Jul. 1989).

(List continued on next page.)

*Primary Examiner*—Jeffrey E. Russel
*Attorney, Agent, or Firm*—Browdy and Neimark

[57] ABSTRACT

An agent which contains, as effective ingredients, interferon-γ and a biologically active substance with either or both activities of promoting production of platelets and leukocytes. A small amount of the agent effectively promotes platelet and/or leukocyte production in mammals including humans without causing side effects.

23 Claims, 8 Drawing Sheets

OTHER PUBLICATIONS

Motoyoshi, Kazuo. "Hematopoietic growth factor (IL–3, G–CSF, GM–CSF, M–CSF, EPO)", The Third Department of Internal Medicine, National Defense Medical College, pp. 275–280 (1967), Abstract only.

Kanz, L. et al., "Hematopoietins in Clinical Oncology", Am. J. Clin. Oncol., vol. 14, suppl. 1, pp. S27–S33 (1991).

De Sauvage, Frederic et al., "Stimulation of Megakaryocytopoiesis and Thrombopoiesis by the C–Mpl Ligand", Nature, vol. 369, pp. 533–5338 (Jun. 16, 1994).

Wendling, Francoise et al., "C–Mpl Ligand is a Humoral Regulator of Megakaryocytpoiesis", Nature, vol. 369 pp. 571–574 (Jun. 16 1994).

Lok, Si et al., "Cloning and Expression of Murine Thrombopoietin cDNA and Stimulation of Platelet Production in vivo", Nature, vol. 369, pp. 565–574 (Jun. 16 1994).

Bartley, T.D. et al., "Identification and Cloning of a Megakaryocyte Growth and Development Factor that is a Ligand for the Cytokine Receptor Mpl", Cell, vol. 77, pp. 1117–1124 (Jul. 1, 1994).

Ganser, A. et al., "Effect of Long–Term Treatment with Recombinant Human Interleukin–3 in Patients with Myelodysplastic Syndromes", Leukemia, vol. 7, No. 5, pp. 696–701 (1993).

Kurzrock, Razelle. "Phase I of Study of Recombinant Human Interleukin–3 in Patients With Bone Marrow Failure", Journal of Clinical Oncology, vol. 9, No. 7, pp. 1241–1250 (Jul. 1991).

Mazur, Eric et al., "Megakaryocytopoiesis and Platelet Production: a Review", Exp. Hematol., vol. 15, pp. 340–350 (1987).

Hoffman, Ronald. "Regulation of Megakaryocytopoiesis", Blood, vol. 74, No. 4, pp. 1196–1212 (1989).

Kimura, Ikuro et al., "Hematological Toxicities of Cancer Chemotherapy", Toxicology Forum, vol. 11, No. 2, pp. 112–121 (1988).

Nakoinz et al. Stimulation of Macrophages Antibody–Dependent . . . Cellular Immunology. vol. 116, pp. 331–340, 1988.

Vassiliadis et al. "CSF–1 and Immune Interferon Synergize . . . " Leukemia Research, vol. 15, No. 10, pp. 943–942, 1991.

Muroshi et al., Interferon–γ Enhances Growth Factor–Dependant in Blood, Aug. 15, 1991, vol. 78, No. 4, pp. 1085–1095.

Nagineni et al. Synergistic Effects of Gamma Interferon . . . Clin. Diagn. Lab. Immun. Sep. 1994, vol. 1, No. 5, pp. 569–577.

Almani et al. Abrogation of Glucocorticosteroid–Mediated Inhibition . . . J. Immunology, May 15, 1991, vol. 146, No. 10, pp. 3523–3527.

Brugger et al. Ex Vivo Expression of Enriched Peripheral Blood . . . Blood May 15, 1993, vol. 81, No. 10, pp. 2579–2584.

Caux et al. Interferon– Enhances Factor–Dependent Myeloid . . . Blood May 15, 1992, vol. 79, No. 10, pp. 2628–2635.

Maciejewski et al. Cytofluorometric and Cytomorphologic . . . Eur. J. Immunology, 1990, vol. 20, pp. 1209–1213.

Murohashi et al. Interferon– Enhances Growth Factor–Dependant . . . Blood Aug. 15, 19891, vol. 78, No. 4, pp. 1085–1095.

Magineni et al. Synergistic Effects of Gamma Interferon . . . Clin. Diag. Lab. Immun. Sep. 1994, vol. 1, No. 5, pp. 569–577.

AGENT FOR PROMOTING THE PLATELET AND THE LEUKOCYTE PRODUCTIONS

BACKGROUND OF THE INVENTION

1. Field of the Invention

The present invention relates to an agent for promoting either or both of the platelet and the leukocyte productions, more particularly, to an agent for promoting either or both of the platelet and the leukocyte productions in mammals including human, which contains as an effective ingredient interferon-γ (hereinafter abbreviated as "IFN-γ") and a biologically active substance(s) with either or both activities of promoting the platelet and the leukocyte productions (hereinafter abbreviated as "biologically active substance(s)", if not specified otherwise).

2. Description of the Prior Art

Platelets exist in mammalian blood, and, for example, human platelets are nuclear cells, 2–3 μm in diameter, and exist in blood in a concentration of about 150,000–400,000 cells/mm$^3$. Human platelets are released from matured megakaryocytes differentiated from pre-megakaryocytes after their proliferation and maturation. The life span of human platelets is about 11 days. Platelets successively contact with damaged endothelial cells in blood vessels, induce the adhesion and the aggregation reactions, and exert hemostasis.

Although the number of platelets in normal human blood is kept within the aforesaid range, it may be lowered by the reduction of platelet productivity in bone marrow, the platelet consumption, the promotion of platelet degradation in periphery, and the abnormal platelet distribution. The platelet reduction is caused, for example, by diseases which directly damage bone marrow such as osteomyelodysplasia, leukemia, cancer metastasis in bone marrow, myelomatosis, Hodgkin's disease, lymphosarcoma, myelofibrosis, myelosclerosis, hypertrophic osteoarthropathy, and osteopetrosis, and by other diseases which damage spleens such as Banti's syndrome, reticulum cell sarcoma, syphilis, and malignant tumors which induce splenomegaly. I. KIMURA and I. TAKAHASHI in "*Toxicology Forum*", Vol.11, No.2, pp.112–121 (1988) reported that the radio- and chemo-therapies used for treating malignant tumors damage bone marrow to cause platelet reduction.

Platelet reduction means a lowering of the function of hemostasis mechanism in vivo which causes skin petechial hemorrhage, rhinorrhagia, tunica mucosa oris hemorrhage, urinary tract hemorrhage, and genitalia hemorrhage, and it may sometimes causes alimentary canal bleeding and intracranial hemorrhage. Furthermore, the platelet reduction gives unfavorable effect on the treatment and the post-treatment of malignant tumors and diseases causative of the platelet reduction.

Blood component transfusion and self- and non-self-bone marrow transplantations are used to treat the platelet reduction. However, these treatments could not be a fundamental therapy for the platelet reduction because the transfusion has a demerit that the life span of platelets is shorter than that of other blood cells, and the transplantations have a demerit that the insertion of transplanted bone marrows is substantially difficult.

Recently, as reported by Ronald Hoffman in "*Blood*", Vol.74, No.4, pp.1,196–1,212 (1989), Erick M. Mazur in *Experimental Hematology*, Vol.15, pp.340–350 (1987), and Hava Avraham in "*Stem Cells*", Vol.11, pp.499–510 (1993), experiments in in vitro systems revealed that the differentiation and maturation of megakaryocytes, which correlate with the platelet level change, is influence by biologically active substances such as interleukin 3 (hereinafter abbreviated as "IL-3"), interleukin 6 (hereinafter abbreviated as "IL-6"), granulocyte colony-stimulating factor (hereinafter abbreviated as "G-CSF"), granulocyte/macrophage colony stimulating factor (hereinafter abbreviated as "GM-CSF"), stem cell growth factor (hereinafter abbreviated as "SCF"), thrombopoietin (hereinafter abbreviated as "TPO"), and erythropoietin (hereinafter abbreviated as "EPO").

Although many trails to increase the platelet productivity by administering biologically active substances to mammals to directly stimulate and grow megakaryocytes or to stimulate the differentiation induction, no satisfactory result is obtained because the growth and differentiation inducibilities of the used biologically active substances are relatively low and because the growth of megakaryocytes in vitro does not necessarily cause the platelet production in vivo.

As reported by Makio OGAWA in "*Blood*", Vol.81, No.11, pp.2,844–2,853 (1993), biologically active substances are generally known to have an activity of promoting the growth and the differentiation induction of megakaryocytes, and an activity of growing blood cell precursors, i.e. an activity of growing neutrophils, lymphocytes, erythrocytes, and mast cells in spleen. Therefore, these substances could not be specific to megakaryocytes: For example, Tadamitsu KISHIMOTO, in "*Blood*", Vol.74, No.1, pp.1–10 (1989) reported that IL-6 induces the maturation of blood cells in general, and L. Kanz et al. in "*American Journal of Clinical Oncology*", Vol.14, Supplement, pp.S27–S33 (1991), and Kazuo MOTOYOSHI in "*Nippon Rinsho*", Vol.50, No.8, pp.1,967–1,972 (1992) reported that EPO induces the maturation of erythrocytes.

Recently, as reported by Frederic J. de. Sauvage et al. in "*Nature*", Vol.369, pp.533–538 (1994), Francoise Wendling et al. in "*Nature*", Vol.369, pp.571–574 (1994), See Rock et al. in "*Nature*", Vol.369, pp.565–568 (1994), and T. D. Bertley et at. in "*Cell*", Vol.77, pp.1,117–1,124 (1994), TPO as a biologically active substance was isolated, revealing that it has an activity of promoting the platelet production. However, the detailed mechanism still remains uncertain. Under these backgrounds, agents for promoting the platelet production, which effectively prevent and/or treat the platelet reduction in mammals including human without causing side effects, have been in great demand.

Leukocytes exist in vertebrate animals' blood and are produced by bone marrows. Normal human blood contains about 4,500–9,500 cells/mm$^3$ of leukocytes which are classified roughly into phagocytes and immunocytes in hematology. Immunocytes include lymphocytes which have a major role of immunological function, while phagocytes include granulocytic cells and monocytic/macrophagic cells which have a phagocytic capacity to prevent vertebrate animals from bacteria, viruses and external substances. Although these Igbanulocytic cells and monocytic/macrophagic cells have a common phagocytic activity, the former first prevents bacteria and viruses, then the latter removes these microorganisms and eliminates the aged and denatured blood cells.

Although the number of leukocytes in normal human blood is kept within the aforesaid range, it may be lowered by the reduction of leukocyte productivity in bone marrow, the excessive exudation of leukocytes into inflammatory tissues and the following leukocytes' destruction, and the excessive consumption of leukocytes by infectious diseases. In addition, the leukocyte reduction is caused, for example, by diseases which directly damage bone marrow such as osteomyelodysplasia, aplastic anemia, leukemia, cancer metastasis in bone marrow, myelomatosis, Hodgkin's disease, lymphosarcoma, myelosclerosis, hypertrophic osteoarthropathy, and osteopetrosis, and other diseases which damage spleens and livers such as Banti's syndrome, reticulum cell sarcoma, syphilis and malignant tumors with splenomegaly.

Leukocyte reduction means a lowering of the function of hemostasis mechanism in vivo and gives unfavorable influence on the treatment and the post-treatment of malignant tumors and diseases causative of leukocytopenia.

Self- and non-self-bone marrow transplantations are used to treat the leukocyte reduction. However, such treatments could not be the fundamental therapy for leukocyte reduction because the insertion of the transplanted bone marrows is substantially difficult.

Recently, as reported by Sucha Nand et al., in "*Blood*", Vol.83, No.2, pp.357–360 (1994), A. Ganser et al., in *Leukemia*, Vol.7, No.5, pp.696–701 (1993), and Razelle Kurzrock et al., in *Journal of Clinical Oncology*", Vol.9, No.7, pp.1,241–1,250 (1991), it was revealed that biologically active substances such as interleukin 3 (hereinafter abbreviated as "IL-3") and granulocyte/macrophage colony stimulating factor (hereinafter abbreviated as "GM-CSF") have an activity of promoting the leukocyte production, and their phase I and phase II clinical trials have been conducted. However, these trials have problems that these biologically active substances could not be administered to some patients because they should be administered to the patients in a relatively large amount of which causes side effects.

Although a variety of medicaments except for the aforesaid biologically active substances have been used as an agent for leukopenia, no satisfactory result has been obtained. Under these backgrounds, agents for promoting the platelet and the leukocyte productions, which effectively prevent and/or treat the symptoms without causing side effects, have been in great demand.

SUMMARY OF THE INVENTION

The present invention is to provide an agent for promoting the platelet and/or the leukocyte productions by using IFN-γ and a biologically active substance(s) which inherently promotes either or both of the platelet and the leukocyte productions in mammals including human.

BRIEF EXAMINATION OF THE ACCOMPANYING DRAWINGS

DETAILED DESCRIPTION OF THE INVENTION

Figure 1:
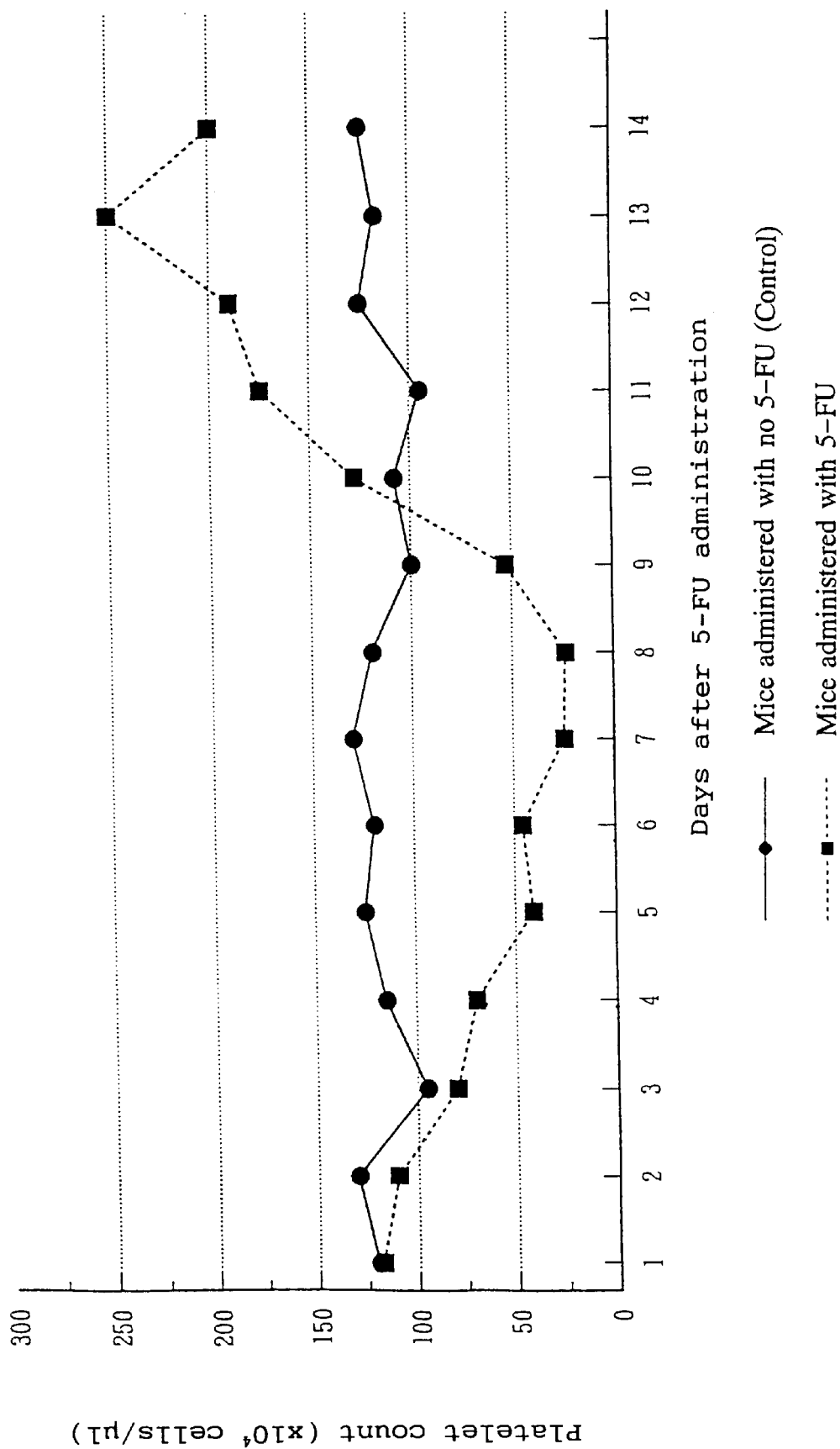
FIG. 1 is a graph of the platelet level change in laboratory mice with thrombocytopenia induced by 5-FU.

The present inventors studied agents for preventing and/or treating thrombocytopenia and leukopenia induced by a variety of diseases and by the radio- and chemo-therapies for treating diseases such as malignant tumors. More particularly, they concentrated upon biologically active substances capable of promoting the platelet and/or the leukocyte productions and studied methods to effectively enhance or augment their activities.

As a result, the present inventors found that IFN-γ, which is known to have antitumor and anti-virus activities, enhances the activity of biologically active substances to promote the platelet and/or the leukocyte productions when administered to mammals together with the substances.

Usually, IFN-γ in itself has neither an activity of promoting the platelet production nor the leukocyte production but on the contrary it induces thrombocytopenia and leukopenia. The present inventors newly found that IFN-γ, when used together with the substances, augments the activity of promoting the platelet and/or the leukocyte productions of the substances to exert their strong activities with only a relatively-low dose of the substances which exerts no such a promoting activity. This means that a combination use of relatively small amounts of IFN-γ and a biologically active substance(s) effectively promotes the platelet and/or the leukocyte productions. Considering that the administration of a relatively high level dose of IFN-γ and biologically active substances causes side effects as a demerit, the present invention has an advantageous feature.

The IFN-γs incorporated in the present agent include, for example, natural IFN-γs produced from human and mammalian leukocytes and established cell lines which are capable of producing IFN-γs, and recombinant IFN-γs obtained by introducing genes coding for IFN-γs derived from these leukocytes and cell lines by recombinant technology into animal cells and microorganisms such as *Escherichia Coli*. Highly purified IFN-γ preparations with a purity at least $1\times10^7$ units/mg protein can be used in the present invention, and crude IFN-γ preparations containing pharmaceutically acceptable impurities can be also used in the present invention as long as they attain the present object. Mixtures of two or more different types of IFN-γ preparations can be used in the present invention to meet to final use. In view of the species specificity and antigenicity of IFN-γs, human IFN-γs are preferably administered to human, and IFN-γs from the same species are suitably administered to animals.

The biologically active substances used in the present invention include IL-3, IL-6, G-CSF, GM-CSF, SCF, TPO, EPO, and macrophage colony stimulating factor (hereinafter abbreviated as "M-CSF"). Any one of these substances with a specific activity at least $1\times10^7$ units/mg protein and other crude natural and recombinant preparations, which are derived from human and other animals and contain pharmaceutically acceptable impurities, can be used in the present invention as long as they attain the present object. If necessary, two or more of these biologically active substances can be used in combination. To administer these substances to human, those derived from human are preferably administered to human, and those derived from the same species of animals are preferably administered to the animals because some of these substances have species specificity and antigenicity.

One or more pharmaceutically acceptable carriers, auxiliary agents excipients, adjuvants, stabilizers, and pH-controlling agents can be arbitrarily added to the IFN-γ and biologically active substance(s) as effective ingredients in the present agent.

The stabilizers usable in the present invention are those which can stabilize the IFN-γ and/or biologically active substance(s) in the present agent. For example, one or more saccharides such as glucose, galactose, xylose, fructose, sucrose, maltose, trehalose, neotrehalose, sorbitol, mannitol, maltitol, lactitol, lactosucrose, maltooligosaccharides, polysaccharides, cyclodextrins, dihydroxyethyl starch, dextrin and dextran, salts such as sodium glucuronic acid, phosphates and metal salts, as well as serum albumin, gelatin, amino acids, and non-ionic surfactants, can be used in the present agent. The concentration of these stabilizers excluding non-ionic surfactants is not specifically restricted, usually in the range of 0.01–50 w/w %, preferably, 1–50 w/w %. The concentration of non-ionic surfactants is in the range of 1 $\mu$g to 1 mg, preferably, in the range of 10 $\mu$g to 1 mg per ml of a solution containing the IFN-γ and biologically active substance(s). When the stabilizers are added to the present agent in the above specified concentration, they stabilize usually the IFN-γ and biologically active substance (s) at least 6 months under 4° C. conditions.

The recommended content of the IFN-γ as an effective ingredient in the present agent is one of which augments the activity of biologically active substances, usually about $0.1–10^9$ units per g of the present agent. The biologically active substances are incorporated into the present agent in an amount of about $10–10^{10}$ units per g of the agent. The form of the present agent is chosen from those in the form of an orally or parenterally administrable liquid, paste, powder or solid. Particularly, agents in a parenterally administrable form are preferable. In the case of preparing the present agent into a liquid or paste form, adjust the pH of the final product to a pH of about 4–9, preferably, pH 6–8, so as not to inactivate the IFN-γ and biologically active substances. Independently of the form and conditions, the present agent should be stored in light-shielded cool conditions of 4° C. or lower to keep stably the effective ingredients.

Explaining now the administration method of the present agent, administer orally or parenterally to mammals including human in continuous manner or one to several shots per day $1 \times 10$ to $1 \times 10^7$ units/kg/day of IFN-γ, preferably, $1 \times – 1 \times 10^5$ units/kg/day of IFN-γ, more preferably, $1 \times 10 – 1 \times 10^3$ units/kg/day of IFN-γ, and $1 \times 10^2 – 1 \times 10^8$ units/kg/day of biologically active substance, preferably, $1 \times 10^2 – 1 \times 10^6$ units/kg/day of biologically active substance, more preferably, $1 \times 10^2 – 1 \times 10^4$ units/kg/day of biologically active substance. In the case of oral administration, the form of the present agent is chosen from those in the form of a liquid, paste, tablet, granule, powder, capsule or cataplasm. While in the case of parenteral administration, the form of the present agent is chosen from those in the form of a liquid or solid suitable for intramuscular injection, intravenous injection, subcutaneous injection, intraperitoneal injection, or osmotic pressure pumping method. The administration period is not specifically restricted and appropriately changed depending on the dose and the symptoms of human and animals to be treated.

The following Experiments and Examples explain the present invention in more detail:

EXPERIMENT 1

Activity of promoting the platelet production

Experiment 1-1

Preparation of laboratory animal model with thrombocytopenia

A laboratory animal model with thrombocytopenia was prepared by intraperitoneally administering once to 7-week-old BDF1 female mice, about 20 g weight, 250 mg/kg mouse by weight of 5-fluorouracil (5-FU) dissolved in phosphate buffered saline (pH 7.4). After the administration, blood was collected from the mice, once a day for 14 days after the administration, from their retinal vessels using "UNOPETTE", a microcollection system commercialized by Becton-Dickinson, Division of Becton, Dickinson and Company, New Jersey, USA, and the collected platelets were microscopically counted to monitor the platelet level change. As a control, mice administered with no 5-FU were used. The results were in FIG. 1.

As is evident from FIG. 1, mice with thrombocytopenia can be readily obtained by administering 5-FU to normal mice. In this experiment system, the platelet levels in mice administered with 5-FU successively decreased gradually, increased gradually up to a level higher than the initial level, and decreased gradually to the normal level.

Experiment 1-2

Determination of the dose of biologically active substances which have an activity of promoting the platelet production and give no effect on laboratory mice with thrombocytopenia.

To continuously administer a prescribed amount of a biologically active substance to the mice with thrombocytopenia in Experiment 1-1, "ALZET® MICRO-OSMOTIC PUMP MODEL 1007D", an osmotic-pump commercialized by ALZA Corporation, CA, USA, was embedded in the mice' subcutaneous tissues to allow the biologically active substance dissolved in phosphate buffered saline (pH 7.4) to release continuously to the tissues at the rate of 0.5 $\mu$l/hour. A recombinant mouse IL-3 (rmIL-3) with a specific activity of $2 \times 10^7$ units/mg protein commercialized by Genzyme Corporation, MA, USA, was used as a biologically active substance with an activity of promoting the platelet production, and administered to the mice at a dose of $1 \times 10^3$ units/kg/day or $1 \times 10^5$ units/kg/day, followed by monitoring the platelet level changes in the mice. As a control, phosphate buffered saline free of IL-3 was administered to laboratory mice with thrombocytopenia. As a result, the administration at a dose of $1 \times 10^5$ units/kg/day of rmIL-3 increased the mice' platelet levels, while the administration at a dose of $1 \times 10^3$ units/kg/day of rmIL-3 did not change the mice' platelet levels. The results were in FIG. 2.

Figure 2:
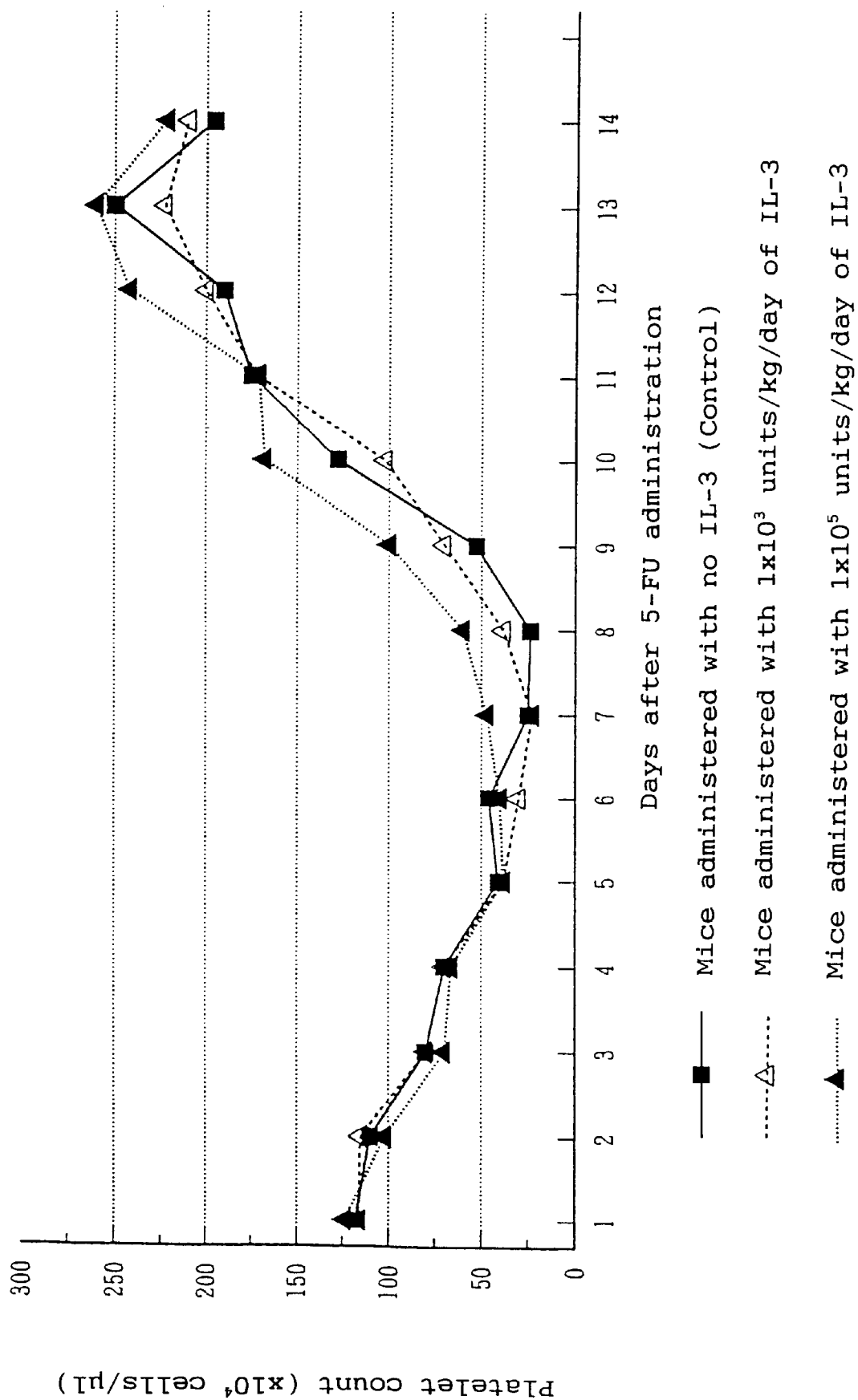
FIG. 2 is a graph of the activity of promoting the platelet production of IL-3 in laboratory mice with thrombocytopenia induced by 5-FU.

As is evident from FIG. 2, the maximum single dose of rmIL-3, which does not increase the mice' platelet levels in mice with thrombocytopenia, was determined to be $1 \times 10^3$ units/kg/day.

Experiment 1-3

Influence of single administration of IFN-γ on platelet level change

To the laboratory mice with thrombocytopenia prepared in Experiment 1-1 were administered a recombinant mouse IFN-γ (rmIFN-γ) with a specific activity of about $1 \times 10^7$ units/mg protein commercialized by Genzyme Corporation, MA, USA, dissolved in phosphate buffered saline (pH 7.4) at a dose of 2.5, $2.5 \times 10$ or $2.5 \times 10^2$ units/kg/day of rmIFN-γ by using an osmotic pump similarly as in Experiment 1-2, followed by monitoring the influence of rmIFN-γ on the platelet level change in the mice. As a control, phosphate buffered saline (pH 7.4) free of IFN-γ was administered to mice with thrombocytopenia. The results were in FIG. 3.

Figure 3:
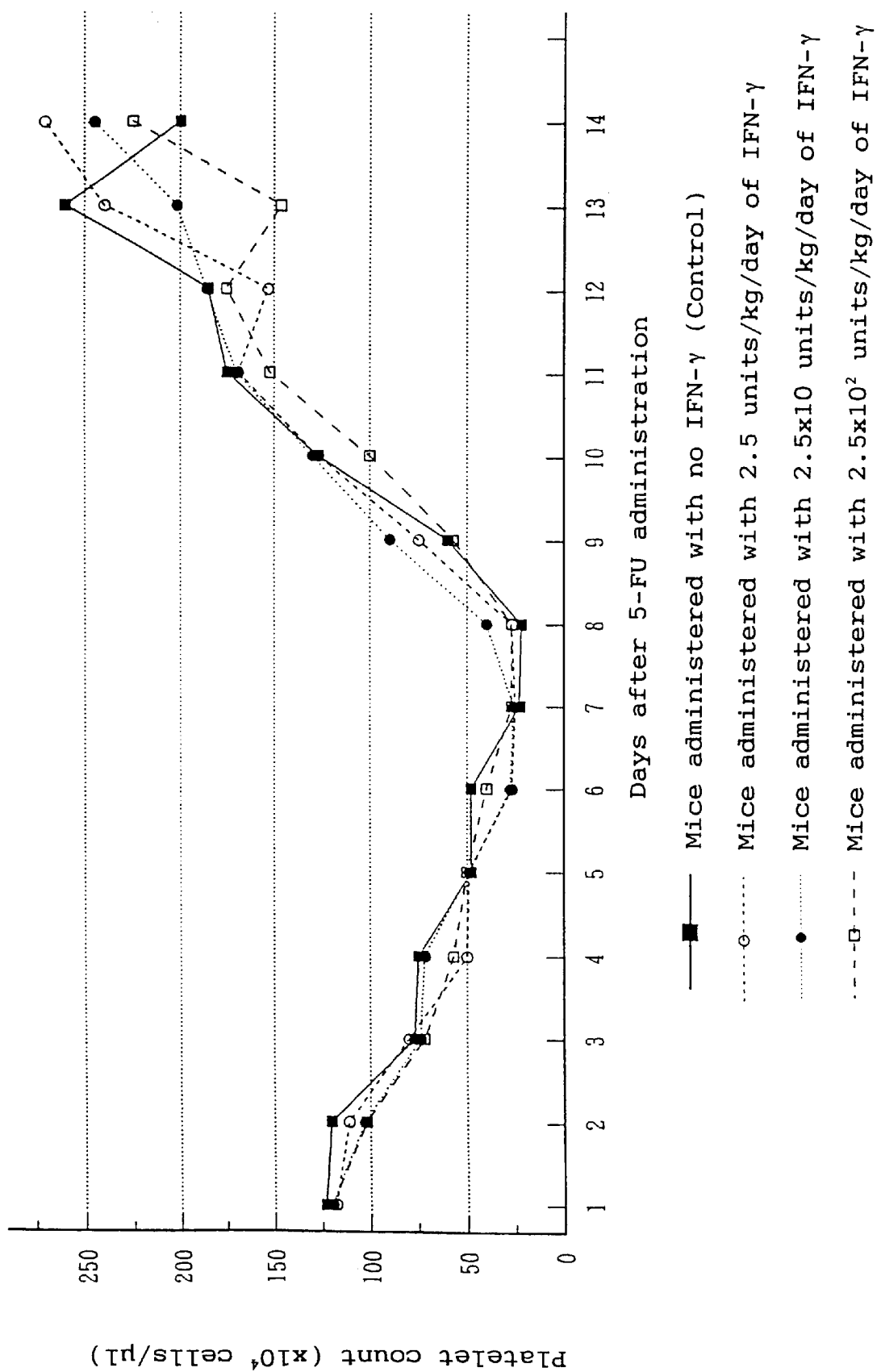
FIG. 3 is a graph of the influence of IFN-γ on the platelet level change in laboratory mice with thrombocytopenia induced by 5-FU.

As is evident from FIG. 3, it was revealed that rmIFN-γ promotes the symptom of mice with thrombocytopenia. This means that rmIFN-γ in itself has no activity of promoting the platelet production in mice, and on the contrary it lowers the platelet level in mice.

Experiment 1-4
Combination administration of IFN-γ and biologically active substance with an activity of promoting the platelet production To the laboratory mice with thrombocytopenia prepared in Experiment 1-1 were administered by the method in Experiment 1-2 a variety of phosphate buffered salines with different concentrations of an IFN-γ preparation and a biologically active substance which promotes the platelet production. The IFN-γ preparation and the biologically active substance used in this experiment were a recombinant mouse IFN-γ (rmIFN-γ) with a specific activity of about $1 \times 10^7$ units/mg protein and a recombinant mouse IL-3 (rmIL-3) with a specific activity of $2 \times 10^7$ units/mg protein, both of which are commercialized by Genzyme Corporation, MA, USA. The doses of the rmIFN-γ and the rmIL-3 were in Table 1.

TABLE 1

| | Experiment No. | Dose (unit/kg/day) | |
|---|---|---|---|
| | | rmIFN-γ | rmIL-3 |
| Laboratory | 1 (Control) | 0 | 0 |
| mice with | 2 | $2.5 \times 10$ | 0 |
| thrombocythemia | 3 | $2.5 \times 10^2$ | 0 |
| | 4 | 0 | $1 \times 10^3$ |
| | 5 | $2.5 \times 10$ | $1 \times 10^3$ |
| | 6 | $2.5 \times 10^2$ | $1 \times 10^3$ |

As a control, phosphate buffered saline (pH 7.4) free of IFN-γ and IL-3 was administered similarly as above to labratory mice imbedded with osmotic pumps. The results were in FIG. 4.

Figure 4:
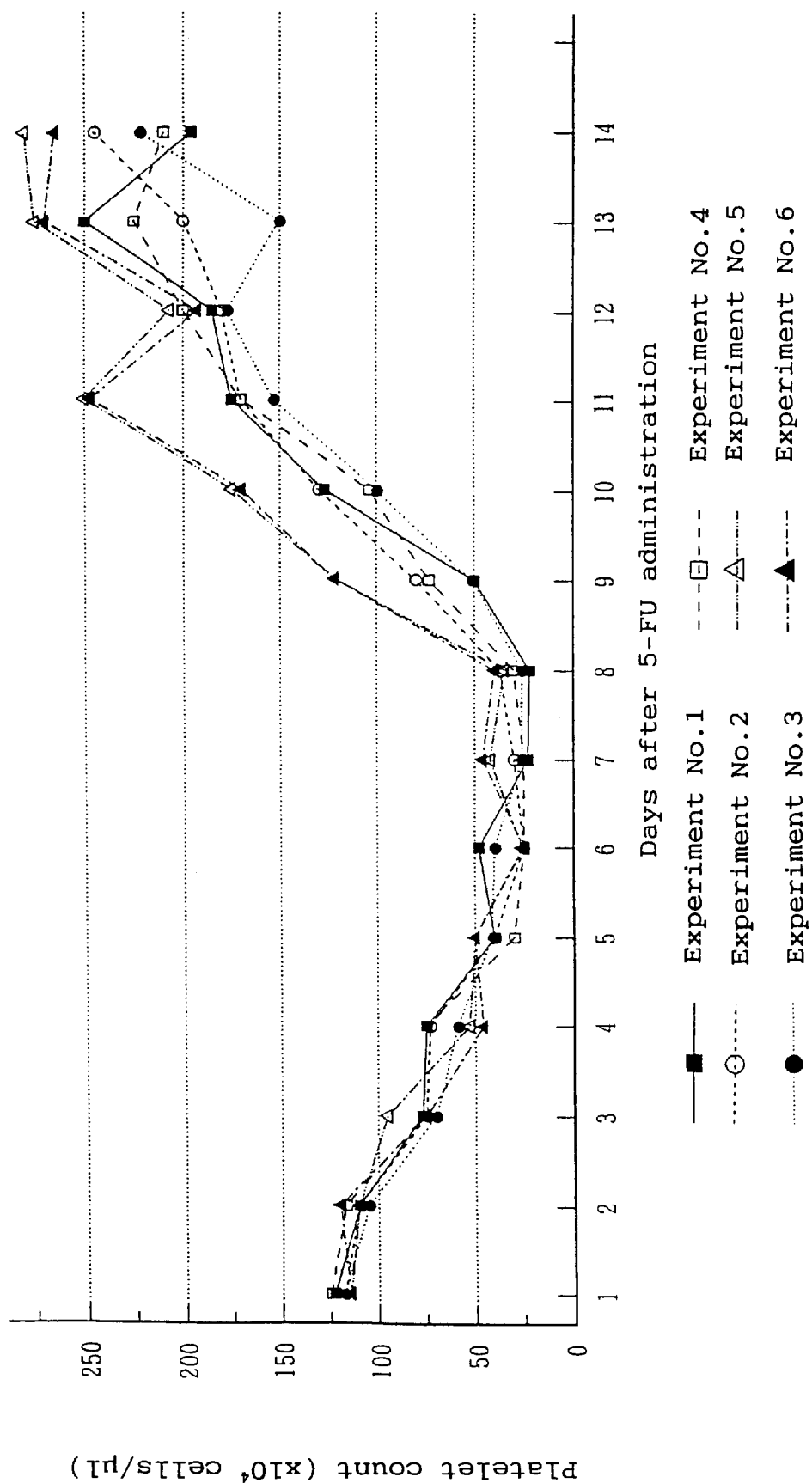
FIG. 4 is a graph of the activity of promoting the platelet production of IFN-γ and IL-3 in laboratory mice with thrombocytopenia induced by 5-FU.

As is evident from FIG. 4, the mice in Experiment No.5 administered with $2.5 \times 10$ units/kg/day of rmIFN-γ and $1 \times 10^3$ units/kg/day of rmIL-3, and the mice in Experiment No.6 with $2.5 \times 10^2$ units/kg/day of rmIFN-γ and $1 \times 10^3$ units/kg/day of rmIL-3 showed that their platelet level began to increase 7 days after the 5-FU administration and remarkably increased 8 days after the administration. While the the mice in Experiments 2 and 3 showed a platelet level reduction depending on the dose of rmIFN-γ similarly as the results in Experiment 1-3. Although the data for 14 days or longer after the 5-FU administration is not shown in FIG. 4, mice with the present agent tended to become the normal level earlier than the mice in Experiment No.1 as a control.

As is not shown concrete data, laboratory mice with thrombocytopenia were administered with a rmIFN-γ preparation selected from a variety of natural and recombinant mouse IFN-γs along with a substance with an activity of promoting the platelet production such as natural and recombinant mouse IL-6, G-CSF, M-CSF, GM-CSF, SCF, EPO or TPO. As a result, similarly as in the above experiment, the mice strongly promoted the platelet production 8 days after the 5-FU administration.

These results show that IFN-γ in itself induces the reduction of the platelet level in mice, but on the contrary it strongly augments the activity of promoting the platelet production of biologically active substances when used together with one or more of the substances.

EXPERIMENT 2
Determination of the amount of IFN-γ and biologically active substance which has an activity of promoting the platelet production Experiment 2-1
Determination of minimum effective dose of IFN-γ

By using the laboratory mice with thrombocytopenia in Experiment 1-1, a recombinant mouse IL-3 (rmIL-3) with a specific activity of $2 \times 10^7$ units/mg protein and a recombinant mouse IFN-γ (rmIFN-γ) with a specific activity of about $1 \times 10^7$ units/mg protein, both of which are commercialized by Genzyme Corporation, MA, USA, were administered by the method in Experiment 1-2 to the mice at a dose of $1 \times 10^{-1} - 1 \times 10^3$ units/kg/day, followed by monitoring the mice' platelet level changes. As a result, the mice administered with rmIL-3 in an amount of which might not induce the platelet production statistically significantly increased the platelet level when administered with rmIL-3 and at least $1 \times 10$ units/kg/day of rmIFN-y. Because of this the minimum effective dose of rmIFN-γ was determined to be $1 \times 10$ units/kg/day.

Experiment 2-2
Determination of minimum effective dose of biologically active substance By using the laboratory mice with thrombocytopenia in Experiment 1-1, a recombinant mouse IL-3 (rmIL-3) with a specific activity of $2 \times 10^7$ units/mg protein and a recombinant mouse IFN-γ (rmIFN-γ) with a specific activity of about $1 \times 10^7$ units/mg protein, both of which are commercialized by Genzyme Corporation, MA, USA, were administered by the method in Experiment 1-2 to the mice at doses of $1 \times 10 - 1 \times 10^4$ units/kg/day of rmIL-3 and $1 \times 10^5$ units/kg/day of rmIFN-γ, followed by monitoring the mice' platelet level changes. As a result, the mice administered with at least $1 \times 10^2$ units/kg/day of rmIL-3 statistically significantly increased the platelet level. Because of this the minimum effective dose of rmIL-3 was determined to be $1 \times 10^2$ units/kg/day. Compared with the results in Experiments 1-2 and 1-4, the dose is less than $\frac{1}{10}$ of the minimum effective dose of rmIL-3 required for promoting the platelet production when used alone.

Although a concrete data is not shown, either a natural or recombinant mouse IFN-γ and either a natural or recombinant mouse IL-6, G-CSF, M-CSF, GM-CSF, SCF, EPO or TPO, which promotes the platelet production, are appropriately used in combination, and, similarly as in the above experiment, administered to laboratory mice with thrombocytopenia, resulting in substantially the same results as in the above experiment.

EXPERIMENT 3
Acute toxicity test

To 7-week-old dd-strain mice, about 30 g weight, was administered subcutaneously or intravenously either a natural human IFN-γ preparation with a specific activity of $1 \times 10^7$ units/mg protein obtained from Hayashibara Biochemical Laboratories, Inc., Oakayama, Japan, or a recombinant human IL-3 preparation with a specific activity of $2 \times 10^7$ units/mg protein commercialized by Genzyme Corporation, MA, USA, at a dose of $1 \times 10^8$ units/kg mouse by weight. As a result, no mouse died. Similarly as above, either a natural or recombinant mouse IFN-γ and either a natural or recombinant mouse IL-6, G-CSF, M-CSF, GM-CSF, SCF, EPO or TPO are appropriately used in combination and administered to mice with thrombocytopenia, resulting in no mouse death. Thus, the present agent for promoting the platelet production is a satisfactory medicament which cause no side effects.

EXPERIMENT 4
Activity of promoting the leukocyte production

Experiment 4-1
Preparation of laboratory animal model with leukopenia

A laboratory animal model with leukopenia was prepared by intraperitoneally administering once to 7-week-old BDF1 female mice, about 20 g weight, 250 mg/kg mouse by weight of 5-fluorouracil (5-FU) dissolved in phosphate buffered saline (pH 7.4). After the administration, blood was collected from the mice, once a day on 1st, 2nd, 4th, 7th, 8th, 9th, 10th and 11th days after the administration, from their retinal vessels using "MICRO-CAPILLARY TUBE", a micro-capillary commercialized by Drummond Scientific, PA, USA, and the collected leukocytes were microscopically counted using "SYSMEX HEMATOLOGY ANALYZER F-820", a blood cell counter commercialized by Toa Medical Electronics Co., Ltd., Hyogo, Japan, to monitor the leukocyte level change. As a control, mice administered with no 5-FU were used. The results were in FIG. 5.

Figure 5:
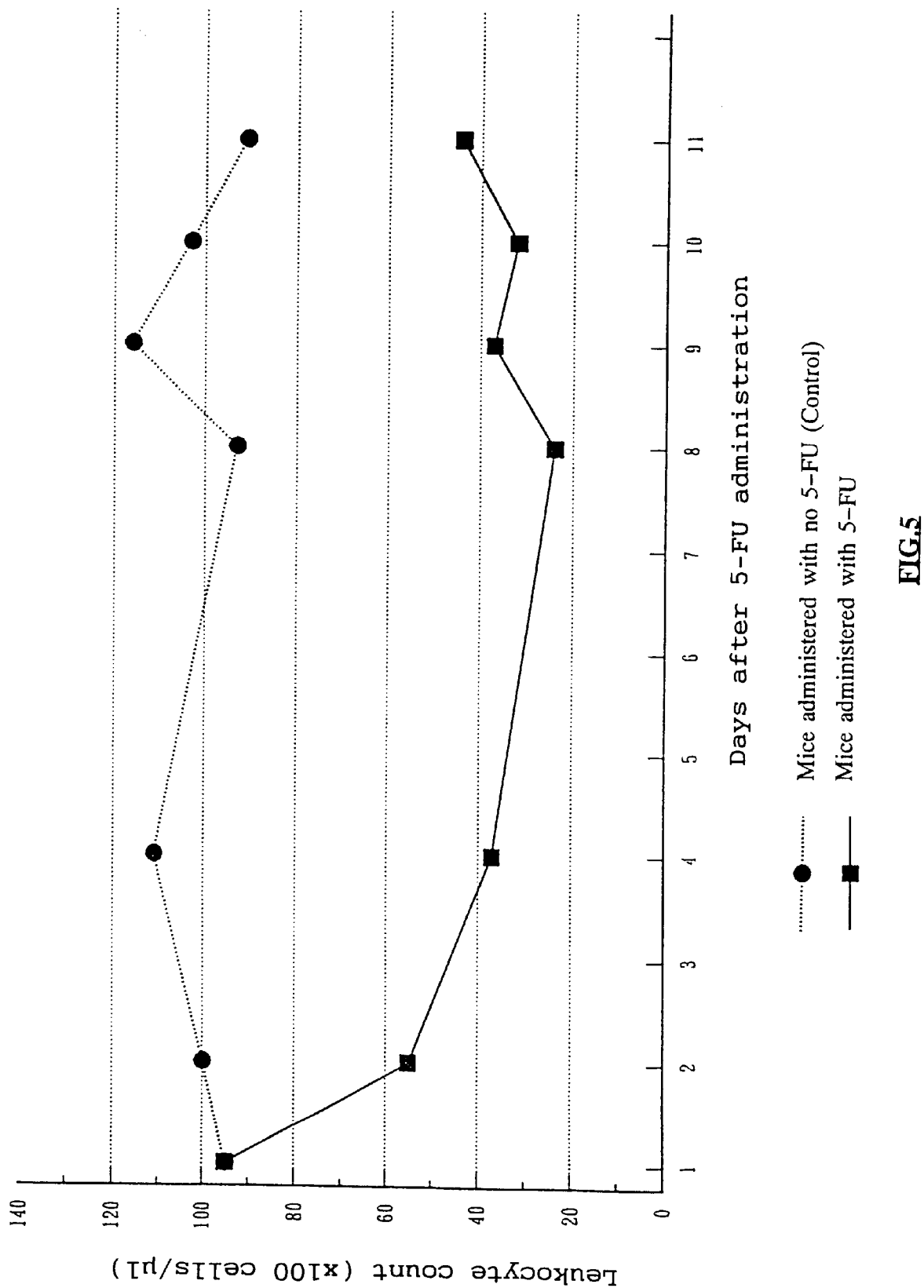
FIG. 5 is a graph of the leukocyte level change in laboratory mice with leukopenia induced by 5-FU.

As is evident from FIG. 5, mice with leukopenia can be readily obtained by administering 5-FU to normal mice. In this experiment system, the leukocyte levels in mice administered with 5-FU decreased gradually and then increased gradually to the normal level.

Experiment 4-2
Determination of the dose of biologically active substances which have an activity of promoting the leukocyte production and give no effect on laboratory mice with leukopenia To continuously administer a prescribed amount of a biologically active substance to the mice with leukopenia in Experiment 4-1, "ALZET® MICRO-OSMOTIC PUMP MODEL 1007D", an osmotic-pump commercialized by ALZA Corporation, CA, USA, was embedded in the mice' subcutaneous tissues to allow the biologically active substance dissolved in phosphate buffered saline (pH 7.4) to release continuously to the tissues at a rate of 0.5 $\mu$l/hour. A recombinant mouse IL-3 (rmIL-3) with a specific activity of $2 \times 10^7$ units/mg protein commercialized by Genzyme Corporation, MA, USA, was used as a biologically active substance with an activity of promoting the leukocyte production, and administered to the mice at a dose of $1 \times 10^3$ units/kg/day or $1 \times 10^5$ units/kg/day, followed by monitoring the leukocyte level changes in the mice. As a control, phosphate buffered saline (pH 7.4) free of IL-3 was administered to laboratory mice with leukopenia. As a result, the administration at a dose of $1 \times 10^5$ units/kg/day of rmIL-3 increased the mice' leukocyte levels, while the administration at a dose of $1 \times 10^3$ units/kg/day of rmIL-3 did not change the mice' leukocyte levels. The results were in FIG. 6.

Figure 6:
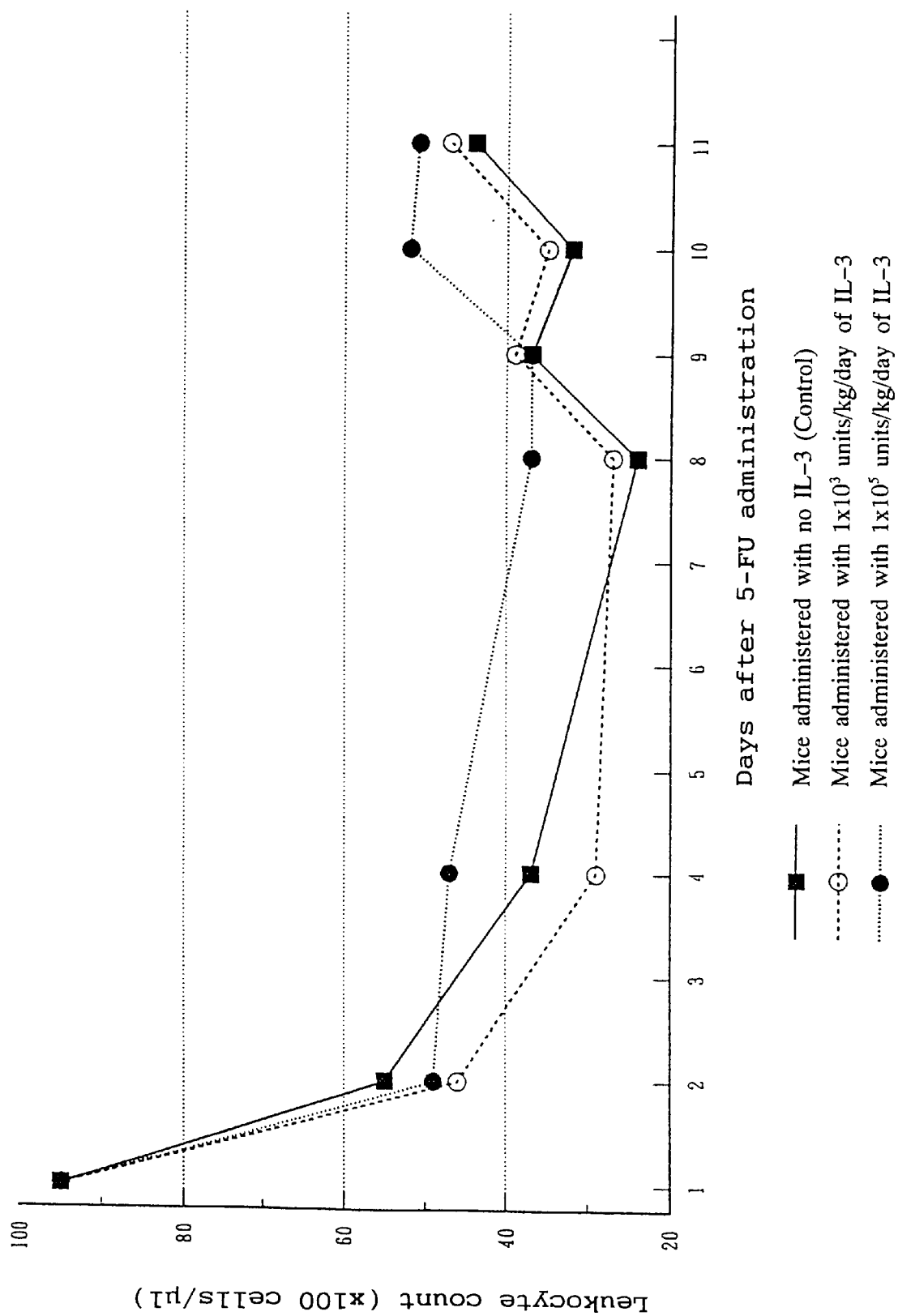
FIG. 6 is a graph of the activity of promoting the leukocyte production of IL-3 in laboratory mice with leukopenia induced by 5-FU.

As is evident from FIG. 6, the maximum single dose of IL-3, which does not increase the mice' leukocyte levels in mice with leukopenia, was determined to be $1 \times 10^3$ units/kg/day.

Experiment 4-3
Influence of single administration of IFN-$\gamma$ on leukocyte level change To the laboratory mice with leukopenia prepared in Experiment 4-1 were administered a recombinant mouse IFN-$\gamma$ (rmIFN-$\gamma$) with a specific activity of about $1 \times 10^7$ units/mg protein commercialized by Genzyme Corporation, MA, USA, dissolved in phosphate buffered saline (pH 7.4) at a dose of $2.5 \times 10$ or $2.5 \times 10^2$ units/kg/day of rmIFN-$\gamma$ by using an osmotic pump similarly as in Experiment 4-2, followed by monitoring the influence of rmIFN-$\gamma$ on the leukocyte level change in the mice. As a control, phosphate buffered saline free of IFN-$\gamma$ was administered to mice with leukopenia. The results were in FIG. 7.

Figure 7:
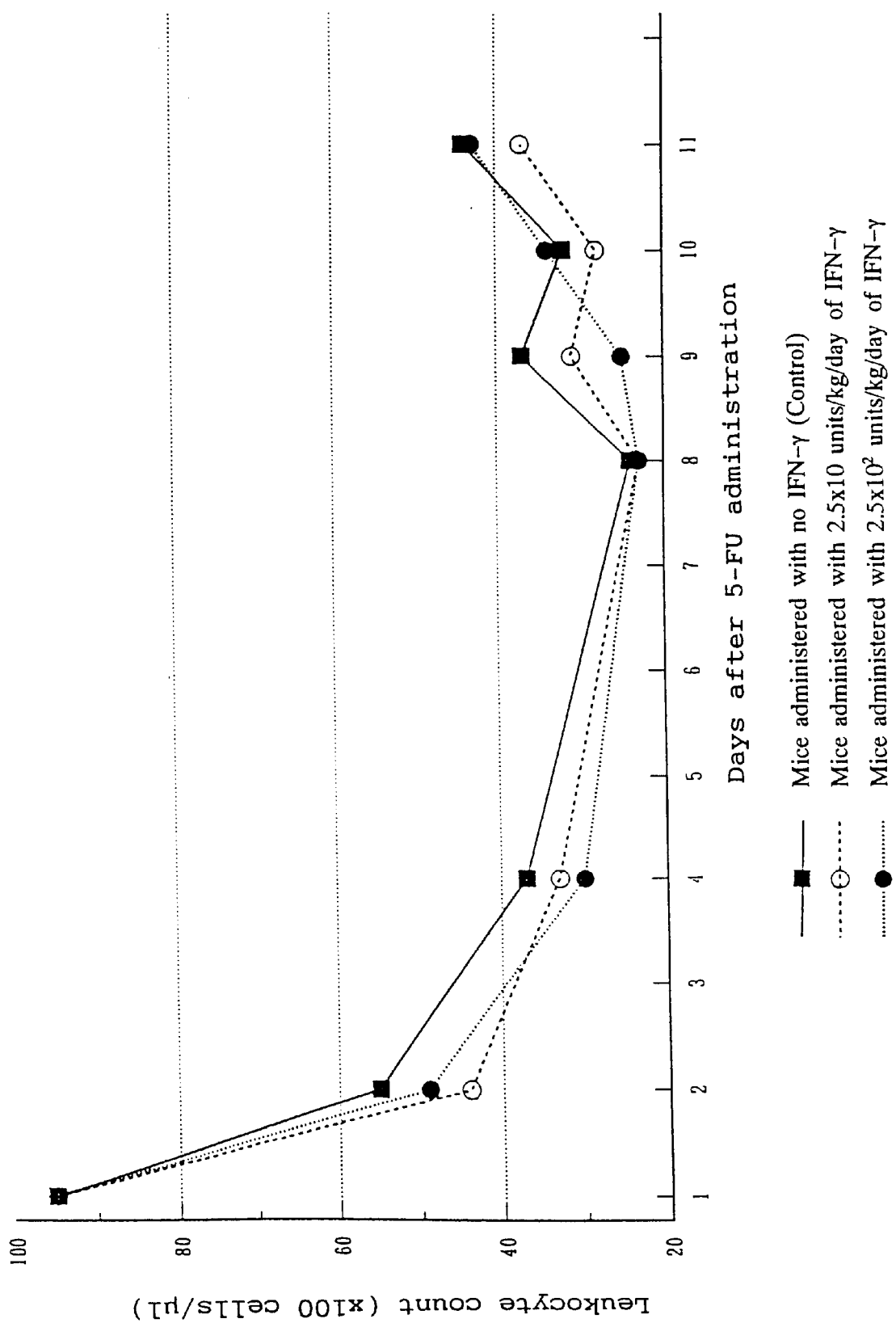
FIG. 7 is a graph of the influence of IFN-γ on the leukocyte level change in laboratory mice with leukopenia induced by 5-FU.

As is evident from FIG. 7, it was revealed that IFN-$\gamma$ promotes the symptom of mice with leukopenia. This means that IFN-$\gamma$ in itself has no activity of promoting the leukocyte production in mice, and on the contrary it lowers the leukocyte level in mice.

Experiment 4-4
Combination administration of IFN-$\gamma$ and biologically active substance with an activity of promoting the leukocyte production To the labroratory mice with leukopenia prepared in Experiment 4-1 were administered by the method in Experiment 4-2 a variety of phosphate buffered salines with different concentrations of an IFN-$\gamma$ preparation and a biologically active substance which promotes the leukocyte production. The IFN-$\gamma$ preperation and the biologically active substance used in this experiment were a combinant mouse IFN-$\gamma$ (rmIFN-$\gamma$) with a specific activity about $1 \times 10^7$ units/mg protein and a recombinant mouse IL-3 (rmIL-3) with a specific activity of $2 \times 10^7$ units/mg protien, both of which are commercialized by Genzyme Corporation, MA, USA. The doses of the rmIFN-$\gamma$ and the rmIL-3 were in Table 2.

TABLE 2

|  | Experiment No. | Dose (unit/kg/day) | |
| --- | --- | --- | --- |
|  |  | rmIFN-$\gamma$ | rmIL-3 |
| Laboratory mice with leukopenia | 1 (Control) | 0 | 0 |
|  | 2 | $2.5 \times 10$ | 0 |
|  | 3 | $2.5 \times 10^2$ | 0 |
|  | 4 | 0 | $1 \times 10^3$ |
|  | 5 | $2.5 \times 10$ | $1 \times 10^3$ |
|  | 6 | $2.5 \times 10^2$ | $1 \times 10^3$ |

As a control, phosphate buffered saline (pH 7.4) free of IFN-$\gamma$ and IL-3 was administered similarly as above to laboratory mice embedded with osmotic pumps. The results were in FIG. 8.

Figure 8:
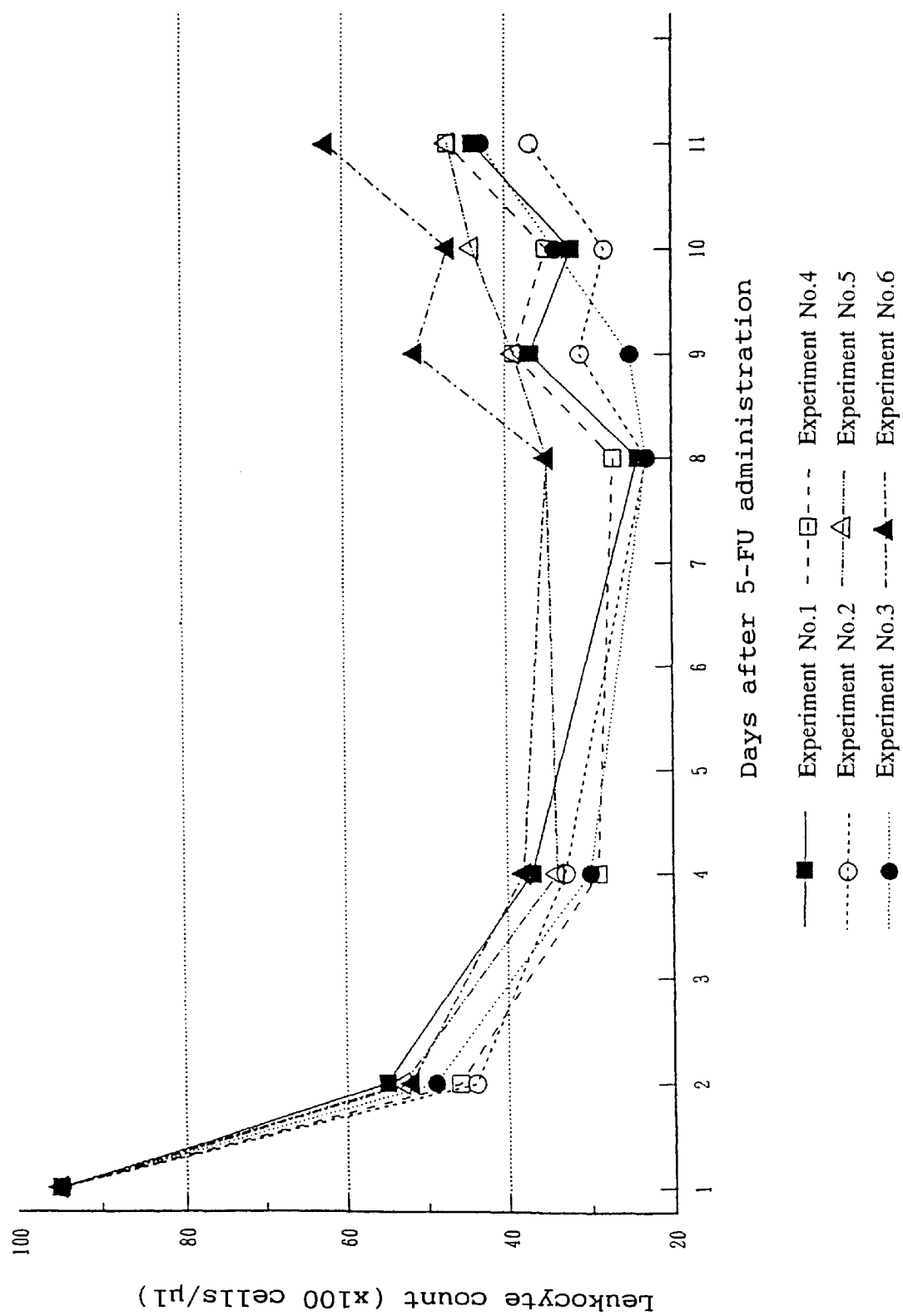
FIG. 8 is a graph of the activity of promoting the leukocyte production of IFN-γ and IL-3 in laboratory mice with leukopenia induced by 5-FU.

As is evident from FIG. 8, the mice in Experiment No.5 administered with $2.5 \times 10$ units/kg/day of rmIFN-$\gamma$ and $1 \times 10^3$ units/kg/day of rmIL-3, and the mice in Experiment No.6 with $2.5 \times 10^2$ units/kg/day of rmIFN-$\gamma$ and $1 \times 10^3$ units/kg/day of rmIL-3 showed that their leukocyte levels significantly increased 8 days after the administration. Although the data for 11 days or longer after the 5-FU administration is not shown in FIG. 8, the mice with the present agent tended to become the normal level earlier than the mice in Experiment No.1 as a control.

As is not shown concrete data, laboratory mice with leukopenia were administered with an IFN-$\gamma$ preparation selected from natural and recombinant mouse IFN-$\gamma$s along with a substance with an activity of promoting the leukocyte production such as natural or recombinant mouse IL-6, G-CSF, M-CSF, GM-CSF or SCF. As a result, similarly as in the above experiment, the administration strongly induced the leukocyte production in the mice 8 days after the 5-FU administration.

These results show that IFN-γ in itself induces the reduction of the leukocyte level in mice, but on the contrary it strongly augments the activity of promoting the leukocyte production of biologically active substances when used together with one or more of the substances.

EXPERIMENT 5
Determination of the amount of IFN-γ and biologically active substance which has an activity of promoting the leukocyte production

Experiment 5-1
Determination of minimum effective dose of IFN-γ

By using the laboratory mice with leukopenia in Experiment 4-1, a recombinant IL-3 (rmIL-3) with a specific activity of $2 \times 10^7$ units/mg protein and a recombinant mouse IFN-γ (rmIFN-γ) with a specific activity of about $1 \times 10^7$ units/mg protein, both of which are commercialized by Genzyme Corporation, MA, USA, were administered by the method in Experiment 4-2 to the mice at a dose of $1 \times 10^{-1} - 1 \times 10^3$ units/kg/day, followed by monitoring the mice' leukocyte level changes. As a result, the mice administered with rmIL-3 in an amount of which might not induce the leukocyte production showed a statistically significant increase of the leukocyte level when administered with the rmIL-3 together with at least $1 \times 10^7$ units/kg/day of rmIFN-γ. Because of this the minimum effective dose of IFN-γ was determined to be $1 \times 10$ units/kg/day.

Experiment 5-2
Determination of minimum effective dose of biologically active substance By using the laboratory mice with leukopenia in Experiment 4-1, a recombinant mouse IL-3 (rmIL-3) with a specific activity of $2 \times 10^7$ units/mg protein and a recombinant mouse IFN-γ (rmIFN-γ) with a specific activity of about $1 \times 10^7$ units/mg protein, both of which are commercialized by Genzyme Corporation, MA, USA, were administered by the method in Experiment 4-2 to the mice at doses of $1 \times 10 - 1 \times 10^4$ units/kg/day of rmIL-3 and $1 \times 10^5$ units/kg/day of rmIFN-γ, followed by monitoring the mice' leukocyte level changes. As a result, the mice administered with at least $1 \times 10^2$ units/kg/day of rmIL-3 showed a statistically significant increase of the leukocyte level. Because of this the minimum effective dose of rmIL-3 was determined to be $1 \times 10^2$ units/kg/day. Compared with the results in Experiment 4-2, the dose is less than 1/10 of the minimum effective dose of rmIL-3 requisite for promoting the leukocyte production when used alone.

Although a concrete data is not shown, either a natural or recombinant mouse IFN-γ and either a natural or recombinant mouse IL-6, G-CSF, M-CSF, GM-CSF or SCF, which promotes the leukocyte production, are appropriately used in combination, and, similarly as in the above experiment, administered to laboratory mice with leukopenia, resulting in substantially the same results as in the above experiment.

EXPERIMENT 6
Acute toxicity test

To 7-week-old dd-strain mice, about 30 g weight, was administered subcutaneously or intravenously either a natural human IFN-γ preparation with a specific activity of $1 \times 10^7$ units/mg protein obtained from Hayashibara Biochemical Laboratories, Inc., Oakayama, Japan, or a recombinant human IL-3 preparation with a specific activity of $2 \times 10^7$ units/mg protein commercialized by Genzyme Corporation, MA, USA, at a dose of $1 \times 10^8$ units/kg mouse by weight. As a result, no mouse died. Similarly as above, either a natural or recombinant mouse IFN-γ and either IL-6, G-CSF, M-CSF, GM-CSF or SCF are appropriately used in combination and administered to mice with leukopenia, resulting in no mouse death. Thus, the present agent for promoting the leukocyte production is a satisfactory medicament which cause no side effects.

EXAMPLE 1

An agent for promoting the platelet and the leukocyte productions was prepared by dissolving in physiological saline for injection a natural human IFN-γ with a specific activity of about $1 \times 10^7$ units/mg protein obtained from Hayashibara Biochemical Laboratories, Inc., Okayama, Japan, and a recombinant human IL-3 with a specific activity of about $2 \times 10^7$ units/mg protein commercialized by Genzyme Corporation, MA, USA, to give concentrations of $2 \times 10^2$ units/ml and $2 \times 10^3$ units/ml, respectively.

The agent can be used as an agent for promoting the platelet and the leukocyte productions for instillation in the prevention and/or the treatment for thrombocytopenia induced by osteomyelodysplasia, aplastic anemia, leukemia, cancer metastasis in bone marrow, myelomatosis, Hodgkin's disease, lymphosarcoma, myelofibrosis, myelosclerosis, hypertrophic osteoarthropathy, osteopetrosis, Banti's syndrome, histiocytic lymphoma, syphilis, and malignant tumors, and for the platelet reduction induced as side effects by the radio- and chemo-therapies used for treating malignant tumors. The agent can be also arbitrarily used as an agent for promoting the platelet production for patients with renal failure.

EXAMPLE 2

A powdery agent for promoting the platelet and the leukocyte productions for injection was prepared by dissolving in physiological saline for injection a natural human IFN-γ with a specific activity of about $1 \times 10^6$ units/mg protein obtained from Japan Chemical Research Co., Tokyo, Japan, and a recombinant human GM-CSF with a specific activity of about $1 \times 10^6$ units/mg protein commercialized by Serva Feinbiochemmica GmbH & Co., Germany, to give concentrations of $1 \times 10^3$ units/ml and $1 \times 10^4$ units/ml, respectively, filtering the solution, and lyophilizing the filtered solution into a powder.

The agent is dissolved in distilled water for injection prior to use. The agent can be used as an agent for promoting the platelet and the leukocyte productions in the prevention and/or the treatment for thrombocytopenia induced by osteomyelodysplasia, aplastic anemia, leukemia, cancer metastasis in bone marrow, myelomatosis, Hodgkin's disease, lymphosarcoma, myelofibrosis, myelosclerosis, hypertrophic osteoarthropathy, osteopetrosis, Bantils syndrome, histiocytic lymphoma, syphilis, and malignant tumors, and for the platelet reduction induced as side effects by the radio- and chemo-therapies used for treating malignant tumors.

EXAMPLE 3

A liquid agent for promoting the platelet and the leukocyte productions was obtained by dissolving in 100 ml of 10 w/v % maltose solution (pH 7.0) containing 100 μg/ml of human serum albumin a recombinant human IFN-γ preparation with a specific activity of about $1 \times 10^6$ units/mg protein commercialized by Japan Chemical Research, Tokyo, Japan, a recombinant human CSF with a specific activity of $1 \times 10^5$ units/mg protein commercialized by Genzyme Corporation, MA, USA, and a recombinant human IL-3 with a specific activity of about $2 \times 10^7$ units/mg protein commercialized by Genzyme Corporation, MA, USA, to give concentrations of $5 \times 10^4$ units/ml, $3 \times 10^5$ units/ml and $5 \times 10^5$ units/ml, respectively.

The product stably retained the activity of human IFN-γ, SCF and IL-3 as effective ingredients for over six months when stored at 4° C. The product can be arbitrarily used as an agent for promoting the platelet and the leukocyte productions in the prevention and/or the treatment for the platelet and the leukocyte reductions induced by some diseases and induced as side effects by the radio- and chemo-therapies.

EXAMPLE 4

An agent for promoting the platelet production for muscular injection was prepared by dissolving in 100 ml of 10 w/v % sucrose solution (pH 7.0) containing 200 μg/ml gelatin a recombinant human IFN-γ with a specific activity of about $1 \times 10^6$ units/mg protein commercialized by Japan Chemical Research, Tokyo, Japan, and a natural human EPO commercialized by China Newtech Development and Trade Corp., China, to give concentrations of $2 \times 10^2$ units/ml and $2 \times 10^6$ units/ml, respectively.

The product stably retained the activity of human IFN-γ and EPO for over six months when stored at 4° C. The agent can be arbitrarily used as an agent for promoting the platelet production in the prevention and/or the treatment for the platelet reduction induced by some diseases and induced as side effects by the radio- and chemo-therapies.

EXAMPLE 5

An agent for promoting the platelet and the leukocyte productions for muscular injection was prepared by dissolving in 100 ml of 10 w/v % sucrose solution (pH 7.0) containing 200 μg/ml gelatin a recombinant human IFN-γ with a specific activity of about $1 \times 10^6$ units/mg protein commercialized by Japan Chemical Research, Tokyo, Japan, and a recombinant human IL-3 with a specific activity of about $2 \times 10^7$ units/mg protein commercialized by Genzyme Corporation, MA, USA, to give concentrations of $2 \times 10^2$ units/ml and $2 \times 10^4$ units/ml, respectively.

The agent can be used as an agent for promoting the platelet and the leukocyte productions in the prevention and/or the treatment for leukopenia induced by osteomyelodysplasia, aplastic anemia, leukemia, cancer metastasis in bone marrow, myelomatosis, Hodgkin's disease, lymphosarcoma, myelosclerosis, hypertrophic osteoarthropathy, osteopetrosis, Banti's syndrome, histiocytic lymphoma, syphilis, splenomegaly, malignant tumors with splenomegaly, and the radio- and chemo-therapies used for treating malignant tumors.

EXAMPLE 6

A recombinant human IFN-γ preparation with a specific activity of about $1 \times 10^6$ units/mg protein commercialized by Japan Chemical Research, Tokyo, Japan, a recombinant high-purity human G-CSF commercialized by Sankyo Co., Ltd., Tokyo, Japan, starch and mannitol were mixed and tabletted in usual manner into tablets containing $3 \times 10^3$ units of human IFN-γ and $1 \times 10^4$ units of G-CSF per tablet, 200 mg weight.

The product can be arbitrarily used as an agent for promoting the platelet and the leukocyte productions to prevent and/or treat human thrombocytopenia and leukoperia.

EXAMPLE 7

A natural human IFN-γ preparation with a specific activity of about $1 \times 10^6$ units/mg protein commercialized by Japan Chemical Research, Tokyo, Japan, a recombinant human GM-CSF with a specific activity of $1 \times 10^6$ units/mg protein commercialized by Serva Feinbiochemmica GmbH & Co., Germany, and "FINETOSE®", anhydrous crystalline maltose commercialized by Hayashibara Biochemical Laboratories, Inc., Okayama, Japan, were mixed, and tabletted in usual manner to obtain tablets containing $1 \times 10^4$ units IFN-γ and $1 \times 10^5$ units of human GM-CSF per tablet, 100 mg weight.

The product is stable for over 6 months at ambient temperature and can be arbitrarily used as an agent for promoting the platelet and the leukocyte productions in the prevention and/or the treatment for human thrombocytopenia and leukopenia.

EXAMPLE 8

A powdery agent for promoting the platelet and the leukocyte productions was prepared by mixing in usual manner starch and trehalose with a recombinant human IFN-γ (rhIFN-γ) with a specific activity of about $1 \times 10^6$ units/mg protein commercialized by Japan Chemical Research, Tokyo, Japan, and a recombinant human IL-6 (rhIL-6) commercialized by Austral Biologicals, USA, to give 50 units/g of rhIFN-γ and $3 \times 10^4$ units/g of rhIL-6.

The product stably retained the activity of rhIFN-γ and rhIL-6 for over 6 months even when stored at ambient temperature. The product can be arbitrarily used as an agent for promoting the platelet and the leukocyte productions in the prevention and/or the treatment for platelet reduction caused by diseases and induced as side effects of the radio- and chemo-therapies.

EXAMPLES 9

A recombinant mouse IFN-γ with a specific activity of about $1 \times 10^7$ units/mg protein and a recombinant mouse SCF with a specific activity of $1 \times 10^5$ units/mg protein were dissolved in physiological saline to give concentrations of 50 units/ml and $5 \times 10^4$ units/ml, respectively, to obtain a liquid agent for promoting the platelet and the leukocyte productions.

The product can be arbitrarily used as an agent for promoting the platelet and the leukocyte productions in the prevention and/or the treatment for the mouse thrombocytopenia and leukopenia.

EXAMPLE 10

A liquid agent for promoting the platelet and the leukocyte productions was prepared by dissolving in physiological saline a recombinant mouse IFN-γ with a specific activity of about $1 \times 10^7$ units/mg protein commercialized by Genzyme Corporation, MA, USA, and a recombinant mouse SCF with a specific activity of $1 \times 10^5$ units/mg protein to give $1 \times 10^7$ units/ml and $3 \times 10^5$ units/ml, respectively.

The product can be arbitrarily used as an agent for promoting the platelet and the leukocyte productions in the prevention and/or the treatment for the mouse thrombocytopenia and leukopenia.

EXAMPLE 11

A powdery agent for promoting the platelet production was prepared by mixing in usual manner starch and trehalose with a recombinant mouse IFN-γ with a specific activity of about $1\times10^7$ units/mg protein commercialized by Genzyme Corporation, MA, USA, a recombinant mouse TPO, and a recombinant mouse IL-3 commercialized by Genzyme Corporation, MA, USA, to give $1\times10^6$ units, $2\times10^6$ units and $1\times10^6$ units per g of the agent, respectively.

The product can be arbitrarily used as an agent for promoting the platelet production in the prevention and/or the treatment for the mouse thrombocytopenia.

The present invention was made based on a novel finding that IFN-γ strongly augments the activity of a biologically active substance(s) capable of promoting the platelet and/or the leukocyte productions when administered together with the substance(s) to mammals including human. The present agent, containing IFN-γ and a biologically active substance (s) as an effective ingredient, effectively prevents and/or treats thrombocytopenia and leukopenia caused by diseases and induced as side effects by the radio- and chemo-therapies.

Thus the present invention greatly contributes to this field.

While there has been described what is at present considered to be the preferred embodiments of the invention, it will be understood the various modifications may be made therein, and it is intended to cover in the appended claims all such modifications as fall within the true spirit and scope of the invention.

We claim:

1. A pharmaceutical composition for promoting platelet and/or leukocyte production in a mammal, comprising:

$0.1-10^9$ units of interferon-γ per gram of the pharmaceutical composition and $2\times10^3-10^{10}$ units of a biologically active substance with either or both activities of promoting platelet and leukocyte production per gram of the pharmaceutical composition, consisting of a member selected from the group consisting of interleukin 3 (IL-3), interleukin 6 (IL-6), granulocyte colony-stimulating factor (G-CSF), macrophage colony-stimulating factor (M-CSF), granulocyte/macrophage colony-stimulating factor (GM-CSF), stem cell growth factor (SCF), thrombopoietin (TPO), erythropoietin (EPO), and mixtures thereof, as effective ingredients, and wherein the content of said biologically active substance is less than a level which substantially promotes platelet and/or leukocyte production when used alone in said mammal to which the pharmaceutical composition is to be administered; and a pharmaceutically acceptable carrier, excipient, stabilizer or auxiliary agent.

2. The pharmaceutical composition of claim 1, wherein said interferon-γ is a natural or recombinant interferon-γ.

3. The pharmaceutical composition of claim 1, which is in an orally- or parenterally-administrable form.

4. A method for promoting platelet and/or leukocyte production in a mammal by administering to said mammal a pharmaceutical composition which contains, as effective ingredients $0.1-10^9$ units of interferon-γ per gram of the pharmaceutical composition and $2\times10^3-10^{10}$ units of a biologically active substance with either or both activities of promoting platelet and leukocyte production per gram of the pharmaceutical composition, wherein said biologically active substance contained in said pharmaceutical composition is present in an amount less than a level which substantially promotes platelet and leukocyte production when used alone, said interferon-γ and said biologically active substance being derived from the same species of mammal to which the pharmaceutical composition is to be administered, wherein the effective ingredients are administered at a dose in the range of about $1\times10$ to $1\times10^7$ units/kg/day for interferon-γ and at a dose in the range of about $1\times10^2$ to $1\times10^8$ units/kg/day for said biologically active substance, said biologically active substance consisting of one or more members selected from the group consisting of interleukin 3 (IL-3), interleukin 6 (IL-6), granulocyte colony-stimulating factor (G-CSF), macrophage colony-stimulating factor (M-CSF), granulocyte/macrophage colony stimulating factor (GM-CSF), stem cell growth factor (SCF), thrombopoietin (TP), and erythropoietin (EPO).

5. The method of claim 4, wherein said interferon-γ is a natural or recombinant interferon-γ.

6. The method of claim 4, wherein said pharmaceutical composition further comprises a stabilizer for said interferon-γ and/or said biologically active substance selected from the group consisting of saccharides, salts, amino acids, serum albumin, gelatin, non-ionic surfactants, glucuronic acid, dextran, hydroxyethyl starch, and mixtures thereof.

7. The method of claim 4, wherein said pharmaceutical composition is in orally- or parenterally-administrable form.

8. The method of claim 4, wherein said mammal is a human.

9. A pharmaceutical composition for promoting platelet production in a mammal, comprising, as effective ingredients, $0.1-10^9$ units-of interferon-γ and $10-10^9$ units of thrombopoietin per gram of the pharmaceutical composition, wherein the content of thrombopoietin is less than a level which substantially promotes platelet production when used alone in the mammal to which the composition is to be admiinistered.

10. The pharmaceutical composition according to claim 9, wherein said interferon-γ is a natural or recombinant interferon-γ.

11. The pharmaceutical composition according to claim 9, further comprising a member selected from the group consisting of saccharides, salts, amino acids, serum albumin, gelatin, non-ionic surfactants, glucuronic acid, dextran, hydroxyethyl starch, and mixtures thereof as a stabilizer for said interferon-γ and/or said biologically active substance.

12. The pharmaceutical composition according to claim 9, which is in an orally -or parenterally-administrable form.

13. A method for promoting platelet production in a mammal comprising the step of administering the pharmaceutical composition of claim 9 to a mammal in need thereof.

14. A pharmaceutical composition for promoting platelet and/or leukocyte production in a mammal, comprising:

$0.1-10^9$ units of interferon-γ per gram of the pharmaceutical composition and $2\times10^3-10^{10}$ units of a biologically active substance with either or both activities of promoting platelet and leukocyte production per gram of the pharmaceutical composition, selected from the group consisting of granulocyte colony-stimulating factor (G-CSF), macrophage colony-stimulating factor (M-CSF), granulocyte/macrophage colony-stimulating factor (GM-CSF), thrombopoietin (TPO), and mixtures thereof, as effective ingredients, wherein the content of said biologically active substance is less than a level which promotes platelet and/or leukocyte production when used alone in said mammal to which the composition is to be administered; and a pharmaceutically acceptable carrier, excipient, stabilizer or auxiliary agent.

15. The pharmaceutical composition according to claim 14, wherein said interferon-γ is a natural or recombinant interferon-γ.

16. The pharmaceutical composition according to claim 14, wherein said pharmaceutically acceptable stabilizer is selected from the group consisting of saccharides, salts, amino acids, serum albumin, gelatin, non-ionic surfactants, glucuronic acid, dextran, hydroxyethyl starch, and mixtures thereof.

17. The pharmaceutical composition according to claim 14, which is in an orally -or parenterally- administrable form.

18. A method for promoting platelet production in a mammal comprising the step of administering a pharmaceutical composition comprising:

$0.1–10^9$ units of interferon-γ per gram of the pharmaceutical composition and $2×10^3–10^{10}$ units of a biologically active substance with an activity of promoting platelet production per gram of the pharmaceutical composition, selected from the group consisting of interleukin 3 (IL-3), interleukin 6 (IL-6), granulocyte colony-stimulating factor (G-CSF), macrophage colony-stimulating factor (M-CSF), granulocyte/macrophage colony-stimulating factor (GM-CSF), stem cell growth factor (SCF), thrombopoietin (TPO), erythropoietin (EPO), and mixtures thereof, as effective ingredients, wherein the content of said biologically active substance is less than a level which promotes platelet production when used alone in said mammal to which the composition is to be administered; and a pharmaceutically acceptable carrier, excipient, stabilizer or auxiliary agent.

19. The method according to claim 18, wherein the pharmaceutically acceptable stabilizer is selected from the group consisting of saccharides, salts, amino acids, serum albumin, gelatin, non-ionic surfactants, glucuronic acid, dextran, hydroxyethyl starch, and mixtures thereof.

20. The pharmaceutical composition according to claim 1, wherein said pharmaceutically acceptable stabilizer is selected from the group consisting of saccharides, salts, amino acids, serum albumin, gelatin, non-ionic surfactants, glucuronic acid, dextran, hydroxyethyl starch, and mixtures thereof.

21. A method for promoting platelet and/or leukocyte production in a mammal by administering to said mammal an effective amount of the pharmaceutical composition according to claim 14.

22. The method according to claim 21, wherein said interferon-γ of the pharmaceutical composition is a natural or recombinant interferon-γ.

23. The method according to claim 21, wherein the pharmaceutical composition is in an orally- or parentally- administrable form.

* * * * *